US007746451B1

United States Patent
Wilson et al.

(10) Patent No.: US 7,746,451 B1
(45) Date of Patent: Jun. 29, 2010

(54) ON-CHIP MICROPLASMA SYSTEMS

(75) Inventors: Chester Wilson, Ruston, LA (US); John W. Sweeney, Ruston, LA (US); Kalyani Peri, Birmingham, AL (US); Rajesh Yalavarthy, Sunnyvale, CA (US)

(73) Assignee: Louisiana Tech University Research Foundation, A Division of Louisiana Tech University Foundation, Ruston, LA (US)

( * ) Notice: Subject to any disclaimer, the term of this patent is extended or adjusted under 35 U.S.C. 154(b) by 207 days.

(21) Appl. No.: 11/624,494

(22) Filed: Jan. 18, 2007

Related U.S. Application Data

(60) Provisional application No. 60/760,091, filed on Jan. 18, 2006, provisional application No. 60/760,092, filed on Jan. 18, 2006.

(51) Int. Cl.
*G01N 21/00* (2006.01)
(52) U.S. Cl. .................................................. 356/72
(58) Field of Classification Search .................. 356/300, 356/334, 316, 72; 313/638; 977/775, 776
See application file for complete search history.

(56) References Cited

U.S. PATENT DOCUMENTS

2006/0022136 A1* 2/2006 Moore ........................ 250/309
2006/0051505 A1* 3/2006 Kortshagen et al. ......... 427/212

OTHER PUBLICATIONS

M. Bhaskar, C. Wilson, L.Que, Y. Gianchandani, "A Micro-Fluidic Ultra-Violet Emission Source for Direct Fluorescence of Tryptophan", IEEE EMBS, 2003, 3380-3383.
L. Que, C. Wilson, Y. Gianchandani, "Microfluidic Electrodischarge Devices with Integrated Dispersion Optics for Spectral Analysis of Water Impurities", Journal of Microelectromechanical Systems, 2005, 185-191, vol. 14, No. 2.
J. Sweeney, C. Wilson, "A Dusty Microplasma Spectroscopic Microdevice for On-site Water Chemistry Analysis", Louisiana Materials and Emerging Technologies Conf., Oct. 2006.
C. Wilson, Y. Gianchandani, "LEd-SpEC: Spectroscopic Detection of Water Contaminants Using Glow Discharges from Liquid Microelectrodes", IEEE, 2002, 248-251.
C. Wilson, Y. Gianchandani, "Miniaturized Magnet Nitrogen DC Microplasmas", IEEE Transactions on Plasma Science, 2004, 282-287, vol. 32, No. 1.

(Continued)

*Primary Examiner*—Tarifur Chowdhury
*Assistant Examiner*—Abdullahi Nur
(74) *Attorney, Agent, or Firm*—Jones, Walker, Waechter, Poitevent, Carrere & Denegre, L.L.P.

(57) ABSTRACT

On-chip microplasma discharge devices capable of producing light, including ultraviolet light, capable of detecting atomic and molecular gas, and capable of detecting atomic and molecular contaminants in water samples. The on-chip microplasma discharge devices utilize nanoparticles or magnets to tune or confine microplasma discharges generated by electrodes delivering a voltage to the device. Selective control of the gaseous pressure at a value between atmospheric pressure and a vacuum pressure allows for further refinement of gas or contaminant detection, or for further tuning of the wavelength of the light to be produced.

17 Claims, 11 Drawing Sheets

OTHER PUBLICATIONS

C. Wilson, Y. Gianchandani, R. Arslanbekov, V. Kolobov, A. Wendt, "Profiling and Modeling of DC Nitrogen Microplasmas", Journal of Applied Physics, 2003, 2845-2351, vol. 94, No. 5.

C. Wilson, Y. Gianchandani, "Spectral Detection of Metal Contaminants in Water Using an On-Chip Microglow Discharge", IEEE Transactions on Electron Devices, 2002, 2317-2322, vol. 49, No. 12.

* cited by examiner (e)

ON-CHIP MICROPLASMA SYSTEMS

CROSS-REFERENCE TO RELATED APPLICATION

This application claims the benefit of U.S. Provisional Application No. 60/760,091, filed Jan. 18, 2006, and U.S. Provisional Application No. 60/760,092, filed Jan. 18, 2006, each of which is hereby incorporated by reference herein in its entirety.

STATEMENT REGARDING FEDERALLY SPONSORED RESEARCH AND DEVELOPMENT

This invention was made with government support under Contract No. DAAD19-02-1-0338 awarded by the Defense Advanced Research Projects Agency (DARPA). The government may have certain rights in the invention.

BACKGROUND OF INVENTION

A. Field of the Invention

The present invention relates to a system utilizing on-chip microplasma discharges in a variety of applications, including for sources of light, for detecting and analyzing gas samples, and for detecting and analyzing contaminants in water. The present invention further relates to methods for utilizing on-chip microplasma discharges for generating light, methods for detecting and analyzing gas samples, and methods for detecting and analyzing contaminants in water.

B. Description of Related Art

Numerous efforts exist to utilize small scale on-chip plasmas (also referred to herein as microplasmas) for a variety of purposes, which may include microscale gas detectors and light sources. The present invention improves upon these efforts to present a reliable, affordable, and innovative system for generating light, including ultraviolet spectra, for detecting and analyzing gas samples, and for detecting and analyzing contaminants in aqueous solution.

Plasma-based discharges are used extensively for lighting in the macro-world, for example, neon bulbs and fluorescent lighting are ubiquitous as lighting sources, Small scale pyramidal discharge devices have been reported as micro-scale light sources, but these types of devices produce visible light only. In previous work, the present inventors developed a light source by striking a plasma discharge to metal-salt doped water in a microfluidic channel, see Mitra, B., et al. "Ultra-Violet Emission Source for Direct Fluorescent of Tryptophan," *Proc. Engineering in Medicine and Biology Soc.*, September 2003, pp. 3380-4; C. G. Wilson et al. "Profiling and Modelling of DC Nitrogen Microplasmas," *J. App. Phys.*, 94(5), September 2003, pp. 2845-51, each of which is herein incorporated by reference in its entirety. It is desirable to have an on-chip tunable light source that may operate within a vacuum and that may be used to fluoresce biomolecules and tagged DNA.

In the same manner, impurities or contaminants in water may be detected and analyzed using microplasmas, see C. G. Wilson et al. "Spectral Detection of Metal Contaminants in Water Using an On-Chip Microglow Discharge," *IEEE Trans. Electron Devices*, vol. 49, No. 12, December 2002, pp. 2317-2322; C. G. Wilson and Y. B. Gianchandani, "Led-SpEC: Spectroscopic Detection of Water Contaminants Using Glow Discharges from Liquid Microelectrodes," *Proc. IEEE Conf. on MEMS*, January 2002, pp. 248-51; and L. Que et al. "Microfluidic Electrodischarge Devices with Integrated Dispersion Optics for Spectral Analysis of Water Impurities," *J Microelectromechanical Sys.*, vol. 14, No. 2, April 2005, pp. 185-191, each herein incorporated by reference in its entirety. Such impurities or contaminants may be atomic (such as copper) or molecular (such as phosphorous and calcium). The latter lack large atomic spectral emission lines in the visible region, making them hard to detect by present means. Additionally, water impurities may also exist in small quantities such that detection is difficult. It is desirable to have an on-chip tunable device purporting to detect a broad range of impurities or contaminants in aqueous solution, including at small quantities, by utilizing a preconcentrator (for example, by evaporating the aqueous solution) and with the capability of operation at vacuum levels, used in combination with a spectrometer to detect and analyze water impurities or contaminants (see J. W. Sweeney and C. G. Wilson, "A Dusty Microplasma Spectroscopic Microdevice for On-Site Water Chemistry Analysis," Louisiana Materials and Emerging Technologies Conference, October 2006, Louisiana State University, Baton Rouge, La.; J. W. Sweeney and C. G. Wilson, "Microdevices for On-Site Water Chemistry Analysis," Louisiana Materials and Emerging Technologies Conference, December 2005, Louisiana Tech University, Ruston, La.; each of which is herein incorporated by reference in its entirety).

In addition to micro-scale light sources and water diagnostics, there is also presently a widespread need for the micro-scale detection of explosive gases, spanning from industrial safety to homeland security applications. Plasma emission spectroscopy is one of the most widely used forms of gas detection. However, direct current plasmas are typically preferred for atomic spectroscopy, not molecular spectroscopy, as red and infrared emissions are limited. Because magnetically confined plasmas have higher densities with lower electron energies, it is known that spectral emissions from molecular gases may be optimized by magnetically confining the microplasma. Previous efforts by the present inventors included magnetically enhanced microplasmas utilized to locally etch silicon (see "Miniaturized Magnetic Nitrogen DC Microplasmas," *IEEE Transactions on Plasma Science*, vol. 32, No. 1, February 2004, pp. 282-287, herein incorporated by reference in its entirety). The ability to enhance the parameters of a direct current microplasma using micromagnets is a distinct advantage for developing inexpensive sensing devices on a microscale. Therefore, it is also desirable to utilize such micromagnets within an on-chip tunable gas detector that may operate in combination with a spectrometer to detect and analyze molecular gases in addition to atomic gases.

BRIEF DESCRIPTION OF THE INVENTION

In one embodiment, the present invention provides an on-chip light source comprising a housing, a plurality of nanoparticles within the housing, a means for energizing said nanoparticles, and a means for controlling the gaseous pressure within the housing. In some embodiments, the light source may comprise a transparent substrate with a reservoir, the nanoparticles positioned within the reservoir. In yet other embodiments, the nanoparticles may comprise a material selected from the group consisting of metal oxide, silica oxide, polymer and ceramic, where the metal oxide may be selected from the group consisting of chromium oxide ($Cr_2O_3$), copper oxide (CuO), and iron oxide ($Fe_2O_3$). In yet other embodiments of the light source, the means for energizing the nanoparticles may comprise at least two electrodes connected to a power source, the electrodes of some embodiments being made of metal. In other embodiments, the power source may provide a direct current negative bias voltage of up to 3000 volts to the electrodes, or a voltage in the range from approximately 300 volts to approximately 1500 volts. In some embodiments, the means for controlling gaseous pressure may comprise a vacuum pump in fluid communication with the interior of the housing.

In some embodiments, the present invention provides a light source comprising a reservoir containing a tagging dye bound to biomolecules, a spectrometer and at least two fiber optic cables, wherein the dye reservoir receives ultraviolet spectra from the nanoparticles through a first fiber optic cable, and emits fluorescent spectra through a second fiber optic cable to the spectrometer.

In other embodiments, the present invention provides a plurality of reservoirs within a glass substrate and a glass sealing layer, wherein the nanoparticles are contained within each reservoir. In such embodiments, the means for energizing the nanoparticles may comprise a plurality of anodes, and a plurality of cathodes, such that power may be selectively applied to one or more reservoirs to energize the nanoparticles therein. Other embodiments may further comprise a runner anode, the runner anode engaged with each anode such that power may be applied to the runner anode to energize each anode.

In some embodiments, the present invention provides an on-chip gas detector and analyzer, comprising a housing, at least two magnets positioned within the housing, a means for energizing the area adjacent to the magnets and a means for controlling the gaseous pressure within the housing. In such embodiments, the housing may comprise a substrate, the two magnets engaged with the substrate. In yet other embodiments, the means for controlling the gaseous pressure within the housing may comprise a vacuum pump in fluid communication with the interior of the housing. In other embodiments, the present invention may provide a means to deliver a gas sample to the housing, which may comprise an on-chip through-port. In many embodiments, the magnets may be positioned with their poles facing each other within the substrate and the means for energizing the area adjacent to the magnets may comprise a patterned layer of metal coating the surface of each magnet to form a hollow cathode, an anode, and a power source connected to the cathode and the anode. In many such embodiments, the power source may provide a direct current negative bias voltage in the range of about 300 to about 1500 volts to the cathode and the anode.

In some embodiments, the present invention may provide an on-chip diagnostic device comprising a housing, an aqueous sample positioned within the housing, a plurality of nanoparticles positioned within the housing, a means for removing moisture from the sample and for energizing the nanoparticles, and a means for controlling the gaseous pressure within the housing. In yet other embodiments, the housing may comprise a glass substrate with a reservoir, the nanoparticles positioned within the reservoir. In other embodiments, the means for controlling the pressure within the housing may comprise a vacuum pump in fluid communication with the interior of the housing. Yet other embodiments may provide a means for removing moisture from the sample and for energizing the nanoparticles that may comprise at least two electrodes connected to a power source. In other embodiments, the power source may provide a direct current negative bias voltage in the range from about 300 to about 1500 volts to the electrodes. In many embodiments, the nanoparticles used in the on-chip microplasma device for detecting water contaminants may comprise material selected from the group consisting of silica oxide, ceramic and polymer.

In still other embodiments of the present invention, the on-chip microplasma device may comprise at least one fiber optic cable in communication with a spectrometer, wherein the cable receives light from the detector.

The above summary of the present invention is not intended to describe each illustrated embodiment or every possible implementation of the present invention. The figures and the detailed description which follow, however, do particularly exemplify these embodiments.

Figure 1A:
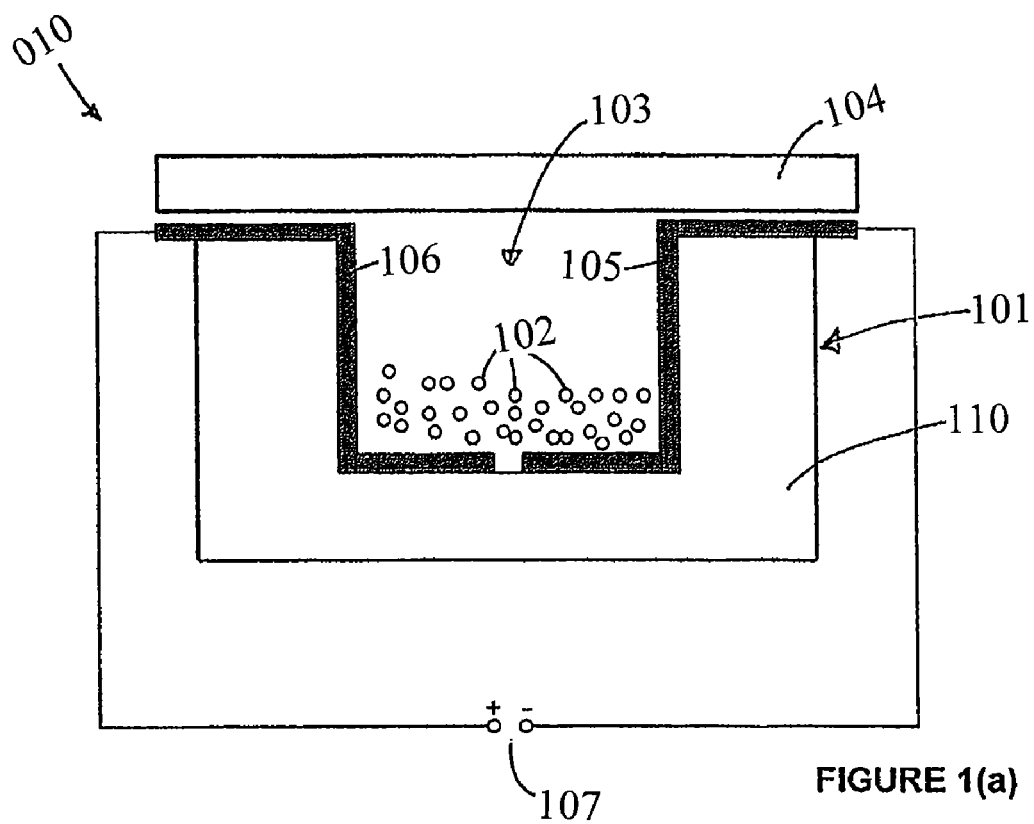
FIGS. 1(a)-1(d) are schematic drawings of one embodiment of the present invention comprising an on-chip light source.
Figure 1B:
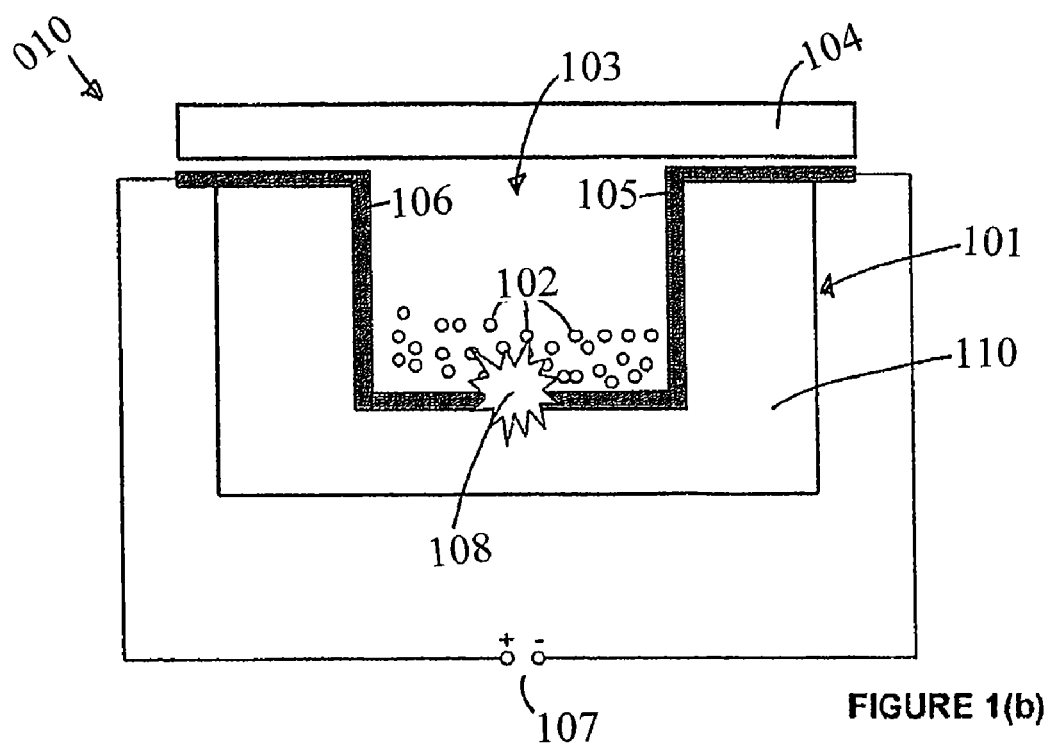

While the invention is amenable to various modifications and alternative foinis, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF INVENTION

Several terms as used herein are intended to have their broadest meanings. The term "microplasma discharge" or simply "microplasma" means any relatively small and highly efficient plasma discharge. The term "nanoparticles" means a microscopic particle with at least one dimension, and whose size is measured in nanometers (nm). It is defined as a particle with at least one dimension <100 nm. The term "micromagnet" means a magnet whose size is measured in millimeters or smaller. The term "electrode" generally means a conductor used to establish electrical contact with a nonmetallic part of a circuit. Although the term "electrode" is used frequently herein, the terms "lead" or "electrical lead" are intended to also mean an electrode and/or its connection to the remainder of the circuit, including to a power supply, such that electrical contact is established through the electrode. The term "microheater" means any device or method known in the art for evaporating a substantial amount of aqueous solution such that contaminants or constituent materials remain at a concentrated level after application of heat or energy, including using electrodes as described herein. The term "housing" as used herein is to be construed broadly, and means any structure devised to enclose, contain or encase embodiments of the present invention. In many embodiments, a housing may comprise simply the substrate upon which the device is built. In other embodiments, a housing may comprise a vacuum chamber wholly enclosing the device or substrate. In yet other embodiments, a housing may comprise a rugged outer container that encloses a vacuum chamber within which the device is situated, or that encloses the device itself while providing a means to control the gaseous pressure within the container.

Figure 7:
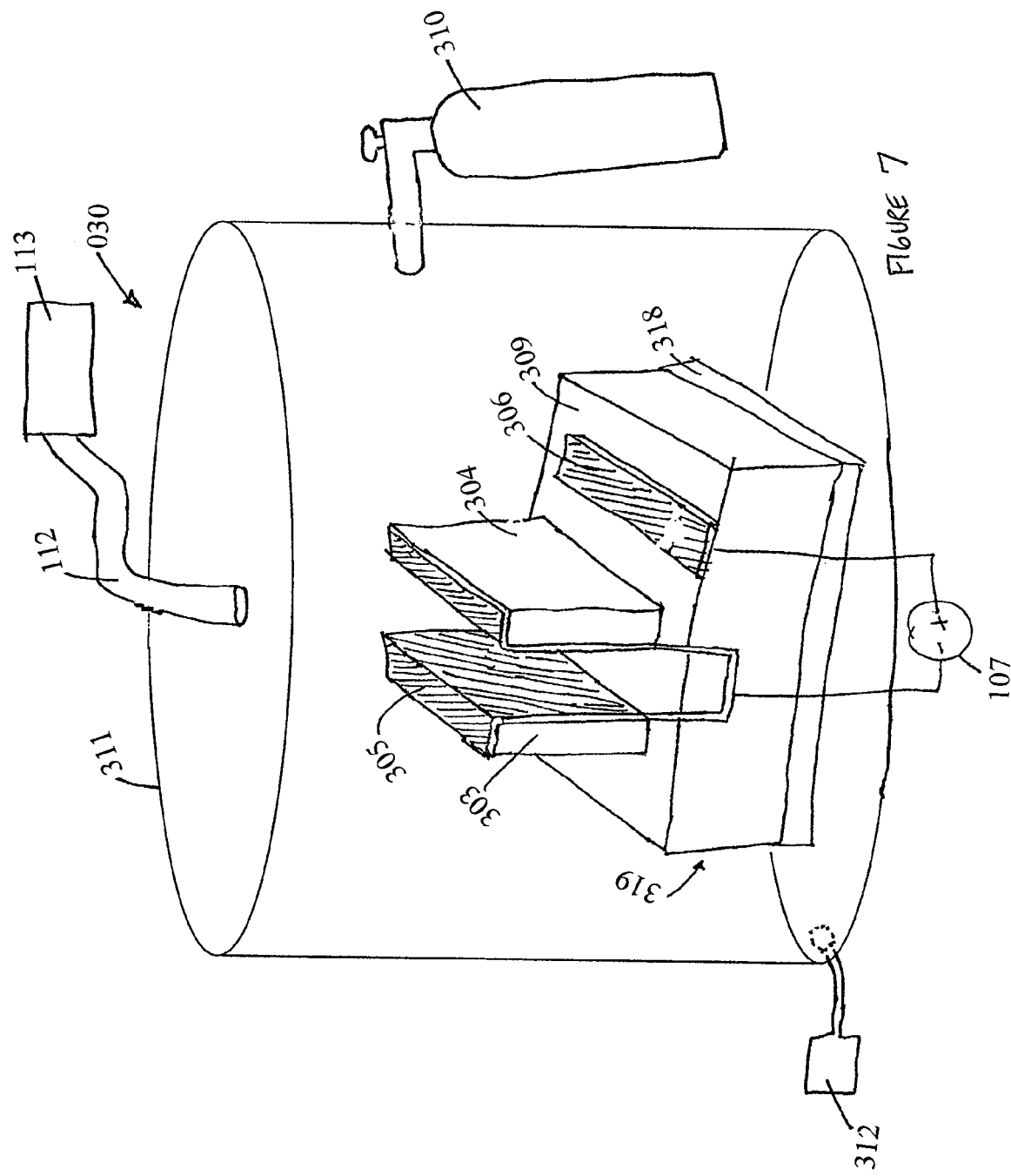
FIG. 7 is a perspective drawing of one embodiment of the present invention comprising an on-chip gas detector.

FIGS. 1(a)-(d) illustrate one embodiment of the present invention. As shown in FIG. 1(a), an on-chip light source 010 comprises a housing 101, electrodes 106, 105, a power source 107, and nanoparticles 102 contained in a reservoir 103 within substrate 110. In some embodiments, housing 101 comprises a substrate 110 and a sealing layer 104 as shown in FIGS. 1(a)-(d). In other embodiments, housing 101 may generally comprise substrate 110 enclosed within a vacuum chamber (as shown generally in FIG. 7). As seen in FIG. 7, vacuum chamber 311 comprises a vacuum pump 312, as is known in the art. Preferably, vacuum chamber 311 is approximately 1 cubic inch (1 in$^3$) in volume and has through-ports for connections to power supply 107. Referring again to FIGS. 1(a)-(d), substrate 110 and sealing layer 104 are formed generally from a transparent material, preferably glass. In some embodiments, substrate 110 may be formed from two or more layered sheets of glass. Substrate 110 has a reservoir 103, preferably formed by sandblasting.

Referring still to FIGS. 1(a)-1(d), electrodes 105, 106 comprise highly conductive materials for carrying electrical signals from power source 107 to energize the nanoparticles 102 within reservoir 103, including but not limited to metals such as chrome, copper, titanium and platinum, patterned onto the surface of substrate 110 by known or future developed methods, some of which are described below. It is preferable that electrodes 105, 106 be constructed from metals with a significant resistance to electroplating, as the potential for some transfer of metal atoms from the electrodes into the microplasma may contaminate the spectral emissions data. It is further preferable that electrodes 105, 106 are fabricated in a manner that withstands intense heat as may be produced by microplasma discharge 108. When a potential difference is applied from power source 107, electrodes 105, 106 serve as cathode 106 and anode 105, with their respective ends exposed to the interior of reservoir 103 to form an analog circuit. Power source 107 comprises any device known in the art to supply a potential difference across the ends of cathode 105 and anode 106 of up to 3000 volts, in certain embodiments. Because of the small scale of the device of the present invention, power source 107 preferably comprises a 12 volt lithium ion battery connected to a high voltage converter that is light weight, consumes low power, and has a wide temperature range (e.g., EMCO High Voltage Corp. Model Q50N-5 (0.125 in$^3$ 5 kV)). In operation, the potential difference applied to cathode 105 and anode 106 is up to 3000 volts, preferably between 300 volts and 1500 volts (or any range therein).

Nanoparticles 102 comprise very small particles ball-milled from commercial off-the-shelf larger particles of varying materials. In those embodiments of the present invention directed to a light source, nanoparticles may preferably comprise metal oxides. In other embodiments, nanoparticles may comprise polymers, ceramics, silica, glass or other materials known in the art to adequately form nanoparticles suitable for doping microplasma discharges.

Figure 10:
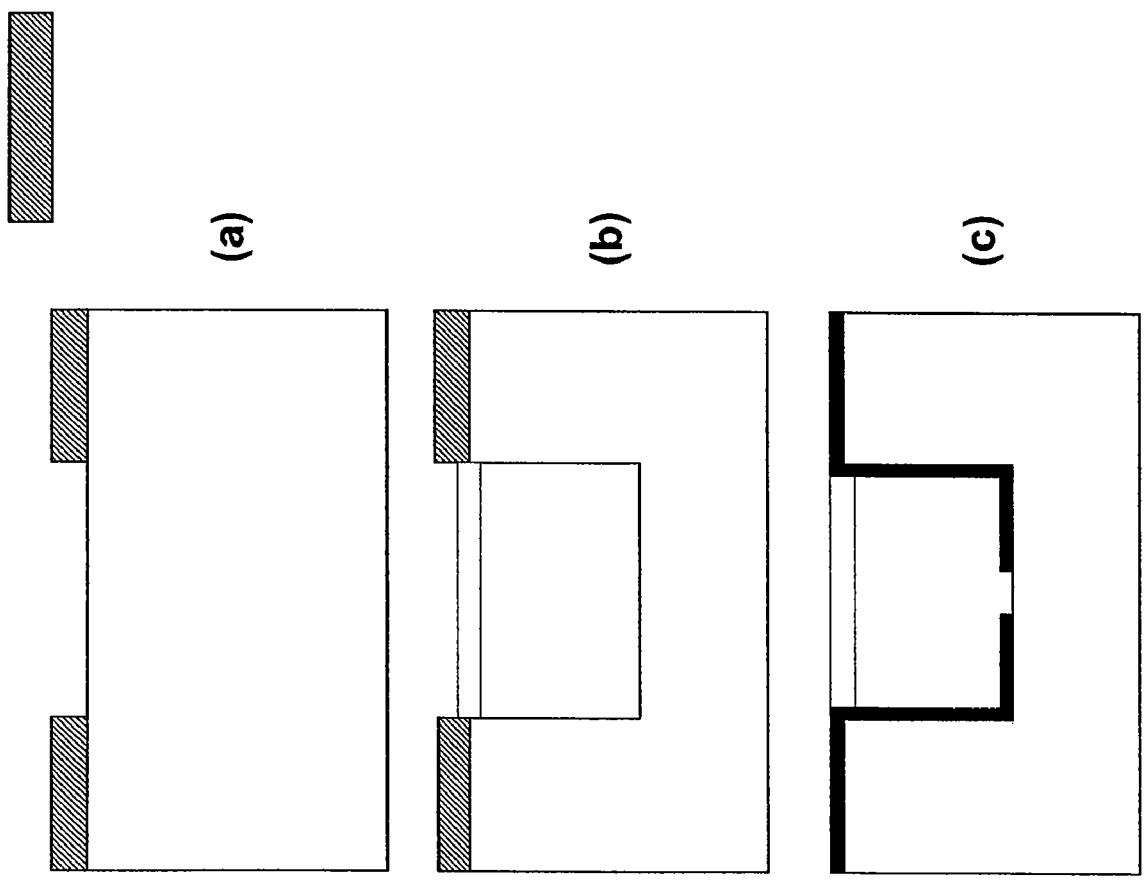
FIGS. 10(a)-10(c) are schematic drawings for fabricating one embodiment of the present invention comprising an on-chip light source.

Referring now to FIGS. 10(a)-(c), an on-chip light source 010 may be fabricated as described herein. In this embodiment, substrate 110 may comprise a block of glass. Substrate 110 preferably measures about 625 cubic millimeters (625 mm$^3$) in volume and more than about 3 millimeters (3 mm) in thickness. A stencil 123, e.g. electrical tape or other materials suitable for stenciling, is applied to the perimeter of substrate 110 to allow for exposure of about 15-20 square millimeters (15-20 mm$^2$) in the center of substrate 110. With stencil 123 in place, substrate 110 may be microsandblasted, using techniques known in the art or any other methods now or future developed, such that reservoir 103 is formed, measuring about 15-20 square millimeters (15-20 mm$^2$) and 3 millimeters (3 mm) deep within substrate 110, as shown in FIG. 10(b). Once reservoir 103 is formed, chrome wires, which serve as electrodes 105 and 106, may be placed along the surface of substrate 110 and into reservoir 103 such that the end of each wire is exposed to the contents of reservoir 103, as shown in FIG. 10(c). The ends of electrode wires 105 and 106 are preferably from about 2 millimeters (2 mm) to about 4 millimeters (4 mm) apart such that when a potential difference is applied to electrodes 105 and 106, microplasmas 108 are confined and energized within reservoir 103. In other embodiments, substrate 110 may be patterned with chrome to form electrodes 105, 106. In these embodiments, after reservoir 103 is formed within substrate 110, a layer of chrome coating may be applied by a thermal evaporation method, as is known in the art. Although chrome is used for the patterned electrodes in this particular embodiment, it should be understood by those in the art that other inert metals, including platinum, titanium and the like, would be preferably suitable to form layers on substrate 110 for patterning electrodes. Photolithography methods, as are well known in the art, and as described below with reference to microheaters in an on-chip diagnostic system within the scope of the present invention, may then be used to create a mask to pattern chrome leads, which serve as electrodes 105 and 106, along the surface of substrate 110 and into reservoir 103 such that the end of each lead is exposed to the contents of reservoir 103. The ends of electrodes 105 and 106 are preferably from about 2 millimeters (2 mm) to about 4 millimeters (4 mm) apart such that when a potential difference is applied to electrodes 105 and 106, microplasmas 108 are confined and energized within reservoir 103. Although wires and patterned electrodes have been described, it should be understood by those skilled in the art that many other shapes and sizes of electrodes are within the scope of the present invention.

Referring now to FIG. 1(a), once electrodes 105 and 106 are in place on substrate 110, reservoir 103 is loaded with nanoparticles, preferably about 0.01 grams (0.01 g) or approximately ten parts per million (10 ppm). Sealing layer 104, preferably a glass sheet sized to coordinate with substrate 110, removably fixes onto the top of substrate 110 such that reservoir 103 is relatively sealed from the influence of outside air. Power supply 107 connects to electrodes 105 and 106 through their ends exiting substrate 110. The system may be placed into vacuum chamber 311, with power supply 107 connections inserted through through-ports therein.

Figure 1C:
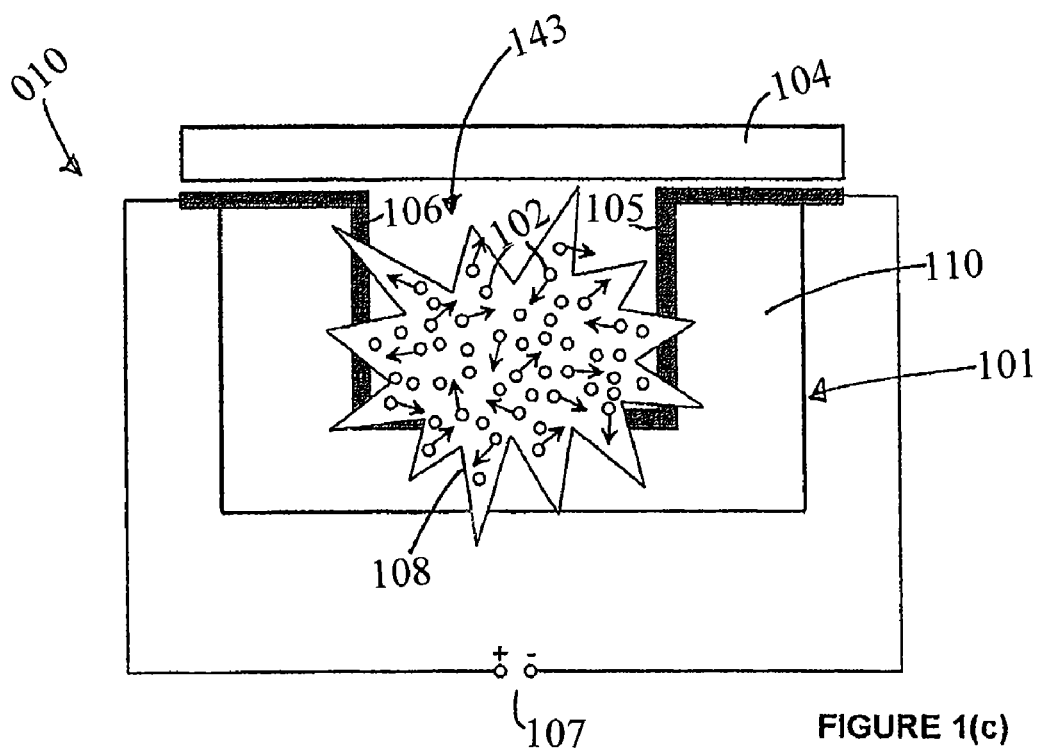
Figure 1D:
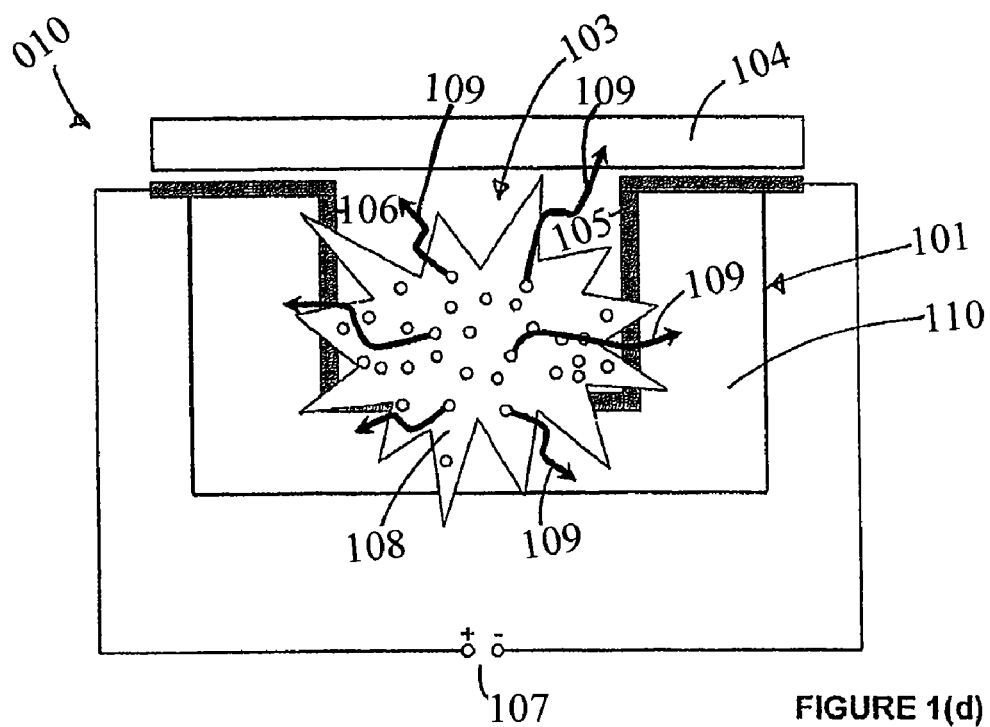

In operation, as shown in FIG. 1(a), a direct current negative bias of about 350 volts to about 1500 volts may be applied by power source 107 to electrodes 105, 106 to create microplasma discharge 108. As suggested in FIG. 1(b), microplasma discharge 108 negatively charges nanoparticles 102. As shown in FIG. 1(c), nanoparticles 102 levitate or sputter into the glow region of microplasma discharge 108. Additional atomic transitions or reaction events change the color of microplasma discharge 108, creating a distinct spectral emission 109, as shown in FIG. 1(d). A full range of very bright discharge colors can be realized by doping with different nanoparticles 102 at different gaseous pressures. At atmospheric pressure, emission is dominated by atomic transitions from nanoparticle 102. By enclosing the system within a vacuum chamber, microplasma discharge 108 may be created within reservoir 103 at levels of gaseous pressure below atmospheric pressure. At these lower gaseous pressure levels, atomic spectral emission disappears from the glow and is replaced by a steady state oxidation/reduction emission. As is known in the art, sheaths form on nanoparticles 102 to repel electrons while oxygen and nitrogen ions accelerate toward nanoparticles 102, producing a reaction molecular spectral emission 109. In this manner, on-chip light source 010 is tunable from atomic to molecular spectral emissions by varying the gaseous pressure level within the device.

Figure 2:
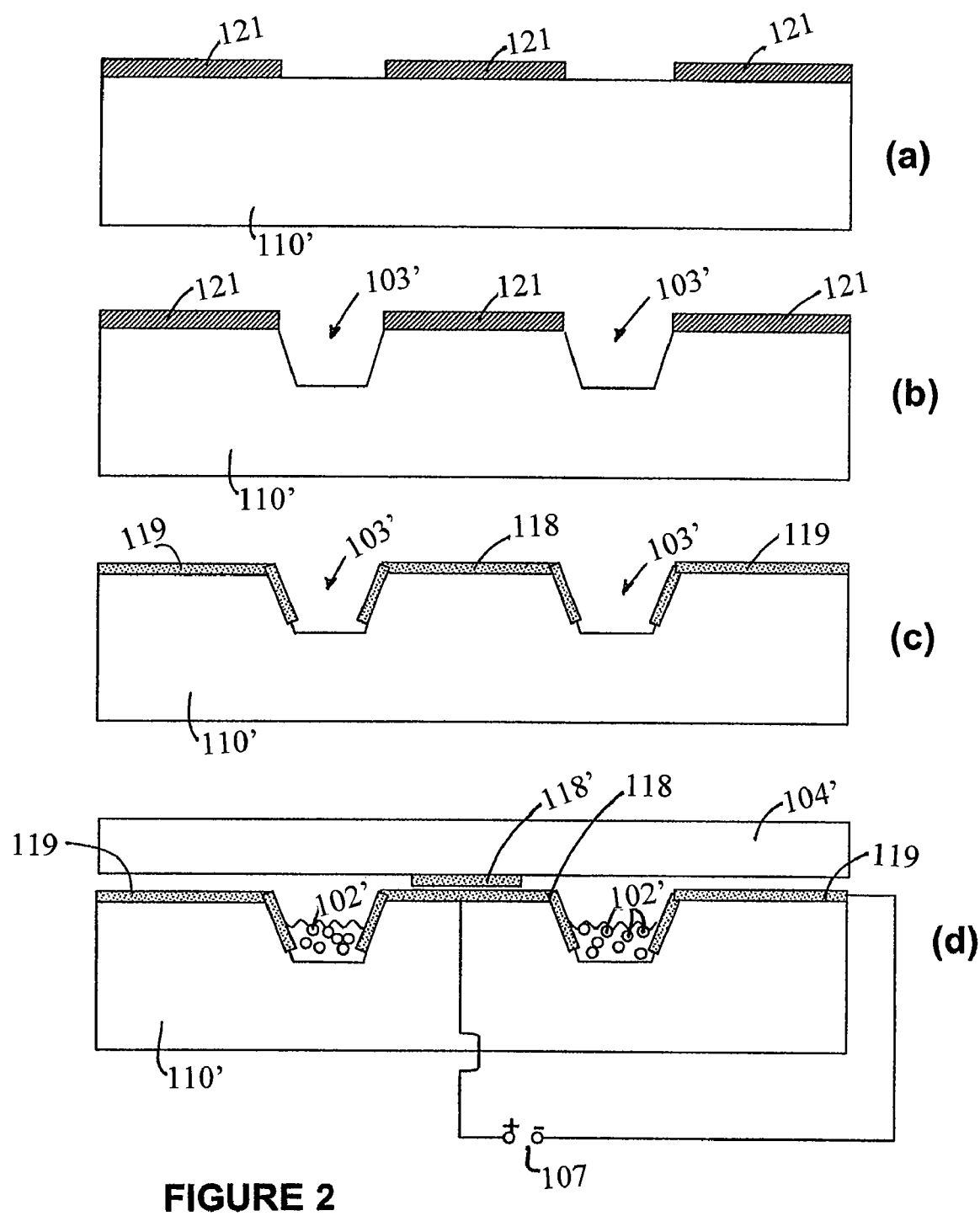
FIGS. 2(a)-2(e) are schematic drawings of one embodiment of the present invention comprising an array of on-chip light sources.
Figure 2E:
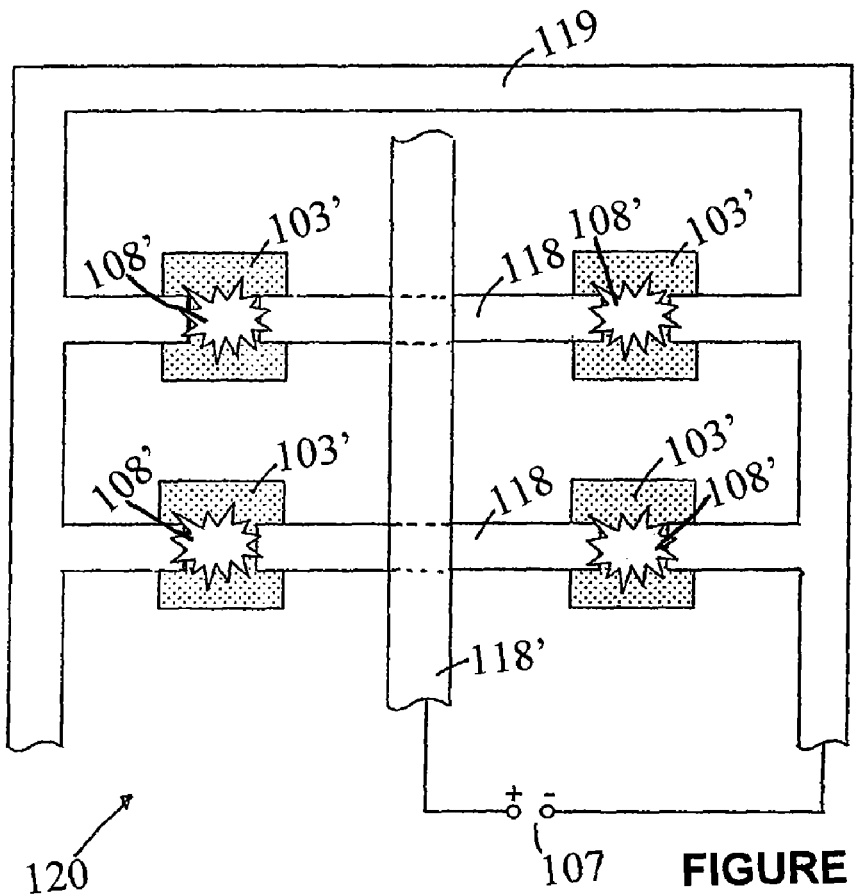

Referring now to FIGS. 2(a)-(e), an on-chip light source 010 comprising multi-cavity arrays may be fabricated as described herein. In this embodiment, substrate 110' may comprise a block of glass. Substrate 110' preferably measures about 144 cubic millimeters (144 mm$^3$) in volume and about 3 millimeter (3 mm) in thickness. As shown in FIG. 2(a), a stencil 121, e.g. electrical tape or other materials suitable for stenciling as are known in the art, is applied to the perimeter of substrate 110' to allow for exposure of a plurality of 1-1.5 square millimeter (1-1.5 mm$^2$) areas within a uniform pattern upon substrate 110' as generally described in FIG. 2(e). Although two rows of reservoirs 103' are depicted therein, it should be appreciated by those with skill in the art that multiple arrangements of arrays with varying numbers of cavities may be fabricated without departing from the scope of the invention. With the stencil 121 in place, as shown in FIG. 2(b), substrate 110' is microsandblasted, using techniques known in the art, such that reservoirs 103' are formed, measuring about 1-1.5 square millimeters (XX mm$^2$) each and 500 micrometeres to 1 millimeters (500 µm-1 mm) deep within substrate 110'. Sealing layer 104', preferably a glass sheet sized to coordinate with substrate 110', removably fixes onto the top of substrate 110'. Once reservoirs 103' are formed, chrome wires, which serve as electrodes 119 and 118, may be placed along the surface of substrate 110' and into reservoirs 103' such that each reservoir 103' receives one end of electrode 119 and one end of electrode 118 and the contents of reservoirs 103' are exposed to each such end, as shown in FIG. 2(d). Although chrome is used for the electrodes in this particular embodiment, it should be understood by those in the art that other inert metals, including platinum, titanium and the like, would be suitable for placement on substrate 110 to act as electrodes. The ends of electrode wires 118 and 119 residing within each reservoir 103' are preferably from about 1.5 millimeters (1.5 mm) to about 2 millimeters (2 mm) apart such that when a potential difference is applied to electrodes 118 and 119, microplasmas 108' are confined and energized within reservoir 103'. Another chrome wire, anode runner 118', which is positioned to be in contact with electrode 118 when the system is in use, may be fixed along the inner surface of sealing layer 104' such that when sealing layer 104' is in place and power supply 107 is connected to the system, electrodes 118 and 118' are in electrical communication with each other and serve as one anode to the array of reservoirs 103', as shown in FIG. 2(d). In other embodiments, substrate 110' and sealing layer 104' may be patterned with chrome electrodes. In these embodiments, after reservoirs 103' are formed within substrate 110', a layer of chrome coating may be applied by a thermal evaporation method, as is known in the art. Photolithography methods, as are known in the art, and as described below with reference to microheaters used in an on-chip diagnostic system within the scope of the present invention, may then be used to create a mask to pattern chrome leads, which serve as electrodes 118, 118' and 119, along the surfaces of substrate 110' and sealing layer 104' and into reservoirs 103' such that the end of each lead 118, 119 is exposed to the contents of reservoirs 103' and such that runner anode 118' is positioned to be in contact with electrodes 118 when the system is in use. The ends of electrode leads 119 and 118 within each reservoir 103' are preferably from about 1.5 millimeters (1.5 mm) to about 2 millimeters (2 mm) apart such that when a potential difference is applied to electrodes 118 and 119, microplasmas 108' are confined and energized within reservoir 103'. Once electrodes 118 and 119 are in place on substrate 110', each reservoir 103' is loaded with nanoparticles 102', preferably about twenty grams (20 g) per reservoir. Reservoirs 103' may contain the same nanoparticles 102', and thus create a uniform array of light when in use, or may be individually loaded with varying types of nanoparticles 102' such that the user directs the types of light emitted from each reservoir 103' by the selection of nanoparticles 102' for reservoirs 103' within the array. Sealing layer 104', preferably a glass sheet sized to coordinate with substrate 110', removably fixes onto the top of substrate 110' such that reservoir 103' is relatively sealed from the influence of outside air and such that runner anode 118' is in electrical communication with electrodes 118 to each reservoir 103'. Power supply 107 connects to electrodes 118' and 119 through their ends exiting substrate 110'. The system may be placed into vacuum chamber 311, with power supply 107 connections inserted through through-ports therein.

In operation of embodiments illustrated, a direct current negative bias of up to 3000 volts, preferably about 300 volts to about 1500 volts (or any range therein) is applied by power source 107 to electrodes 119 and 118' to create microplasma discharges 108' within each reservoir 103' between electrodes 119 and 118, in the same manner as described above with reference to one reservoir. A full range of very bright discharge colors can be realized by doping with different nanoparticles 102' at different gaseous pressures.

Figure 3:
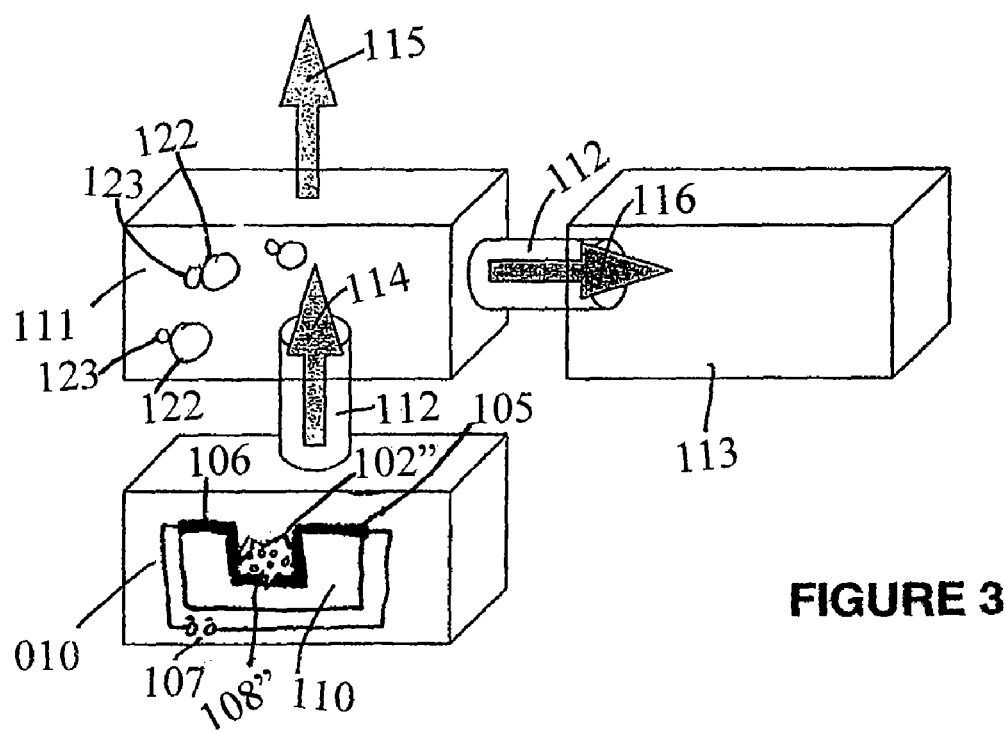
FIG. 3 is a schematic drawing of one embodiment of the present invention comprising an on-chip light source utilized to fluoresce bio-molecules using bio-tagging dye.

Referring now to the embodiment shown in FIG. 3, an on-chip light source 010 may be fabricated as described above and implemented to fluoresce or excite bio-molecule tagging dye 122 for the detection of bio-molecules 123. In this embodiment, the system includes an on-chip light source 010, a sample reservoir 111 holding tagging dye 122 bound to bio-molecules 123, spectrometer 113 (e.g., HR2000CG-UV-NIR High Resolution Spectrometer, Ocean Optics, Inc., Dunedin, Fla.), and fiber optic cables 112. On-chip light source 010 has reservoir 103 containing chrome oxide ($Cr_2O_3$) nanoparticles 102". Although chrome oxide nanoparticles are used in the embodiment described herein, it should be appreciated by those skilled in the art that other metal oxides or nanoparticles, including copper oxide (CuO), iron oxide ($Fe_2O_3$), silica oxide, polymer or ceramics, may be used to fluoresce biomolecules in this manner. Sample reservoir 111 may be fabricated from any materials known in the art, and preferably allows for entry of ultraviolet spectra 114 for fluorescence of tagging dye 122 through fiber optic cable 112 and for exit of fluorescence spectra 116 through fiber optic cable 112 to spectrometer 113. Bio-tagging dye 122, e.g., 7-methoxycoumerin-3-carboxylic acid (e.g., M-1420 MP, Invitrogen Corp., Carlsbad, Calif.) and bio-molecules 123, e.g., DNA, may be jointly prepared and delivered to sample reservoir 111. Spectrometer 113 may be any of those known in the art to measure intensity of the fluorescent spectra 116 as a function of its wavelength, preferably an instrument of a small size to reduce the size of the system overall. Fiber optic cables 112, which are commercial off the shelf cables designed to guide light along their length by total internal reflection, are preferably connected from light source 010 to sample reservoir 111 at right angles, and preferably connected from sample reservoir 111 to spectrometer 113 at right angles, such that the fluorescence spectra 116, which is emitted 90 degrees from incident ultraviolet spectra 114, is maximally transmitted to spectrometer 113.

In operation, as shown in FIG. 3, in the manner described above, microplasma discharge 108" negatively charges chrome oxide nanoparticles 102". Nanoparticles 102" levitate or sputter into the glow region of microplasma discharge 108" to create a distinct Path I ultraviolet spectral emission 114. Ultraviolet spectra 114 travels through fiber optic cable 112 to sample reservoir 111. The ultraviolet components of spectra 114 are absorbed by tagging dye 122 (shown as Path II absorption spectra 115), causing an emission of Path III fluorescent spectra 116. Path III fluorescent spectra 116 travels through fiber optic cable 112 to spectrometer 113, where the intensity of the fluorescent spectra as a function of its wavelength is transmitted to and/or analyzed by end-use equipment, such as microprocessors, computers, and the like.

Figure 4:
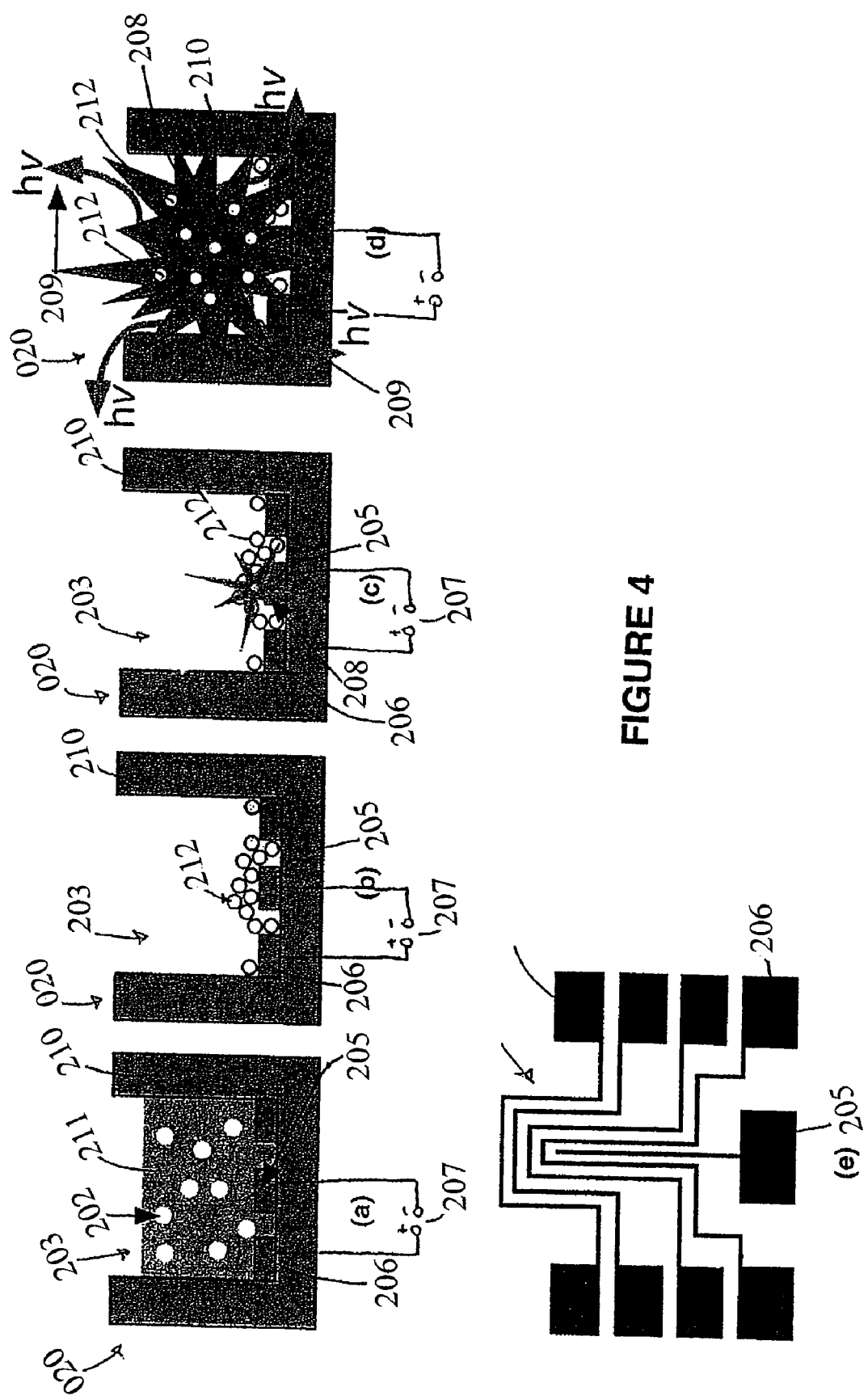
FIGS. 4(a)-4(e) are schematic drawings of one embodiment of the present invention comprising an on-chip water diagnostic system.
Figure 5:
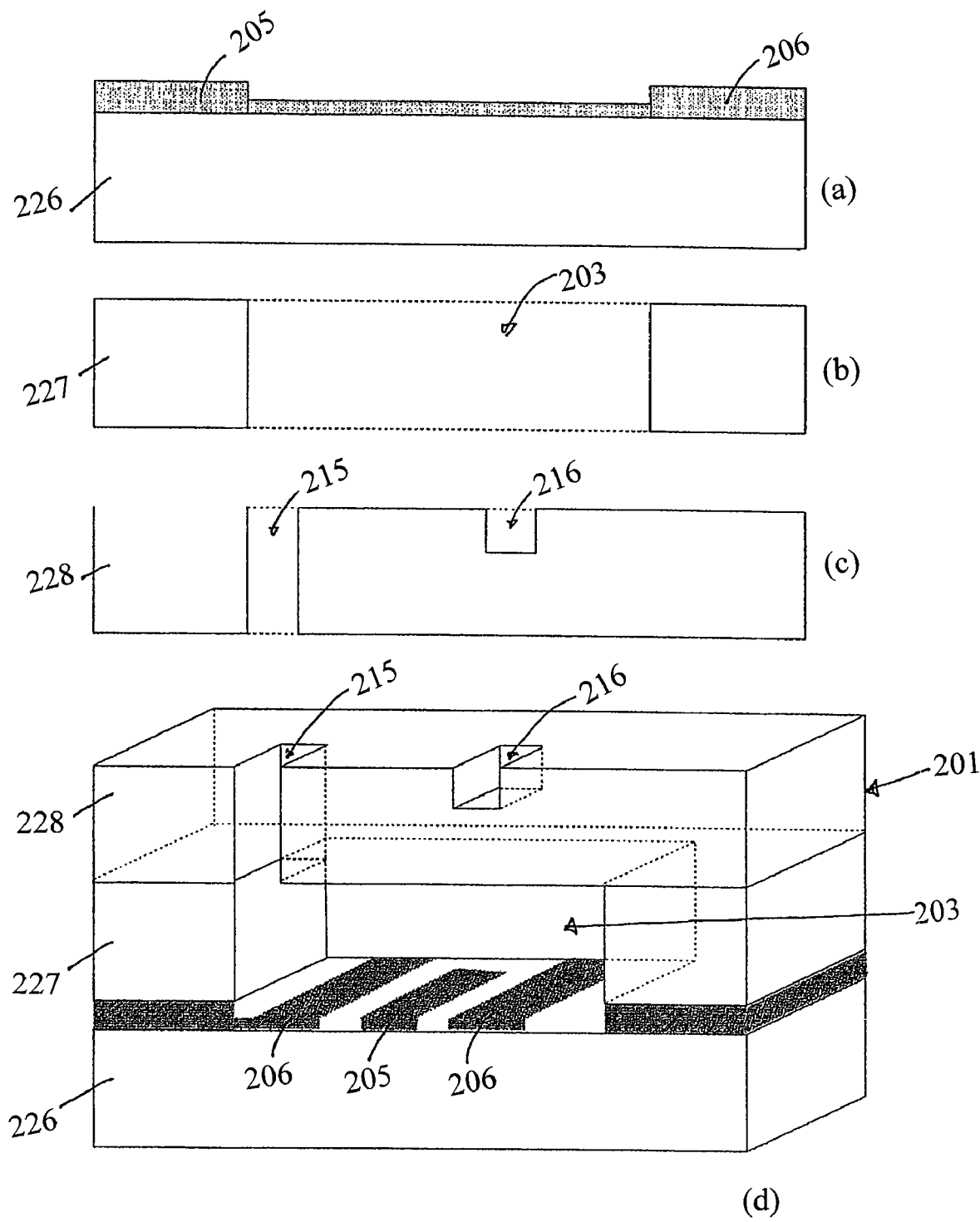
FIGS. 5(a)-(e) are schematic drawings for fabricating one embodiment of the present invention comprising an on-chip water diagnostic system.
Figure 5:
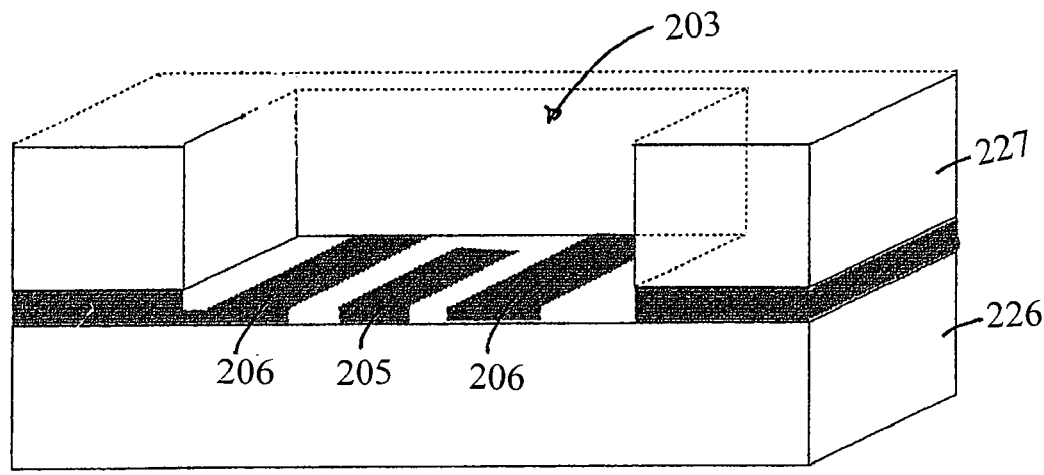
Figure 6:
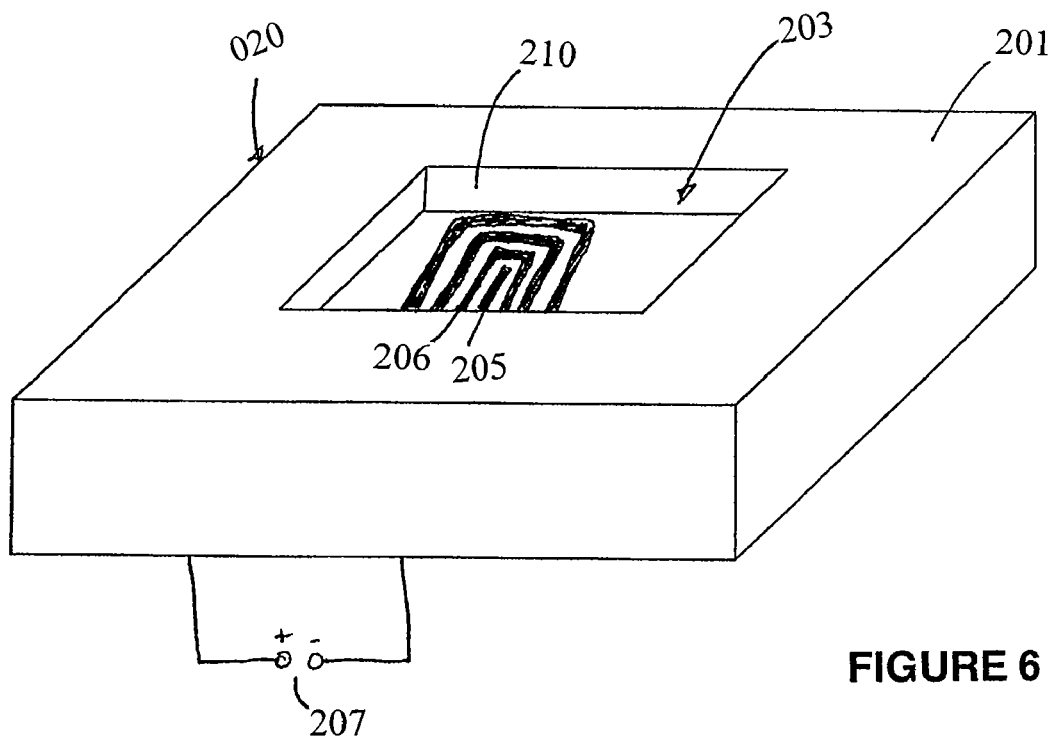
FIG. 6 is a perspective drawing of one embodiment of the present invention comprising an on-chip water diagnostic system.

FIGS. 4, 5 and 6 illustrate another embodiment of the present invention. As shown in FIGS. 4(*a*)-4(*d*), an on-chip water diagnostic system 020 comprises a housing 201, electrodes 205, 206, and power supply 107. In some embodiments, housing 201 comprises a substrate 210. In other embodiments, housing 201 may generally comprise substrate 210 enclosed within a vacuum chamber 311 (as shown generally in FIG. 7). As shown in FIG. 7, vacuum chamber 311 further comprises a vacuum pump 312. Preferably, vacuum chamber 311 is approximately 1 cubic inch (1 in$^3$) in volume and has through-ports for connections to power supply 107. Referring again to FIGS. 4-6, substrate 210 may further comprise at least two layers of glass sheets 226, 227 as described below.

Electrodes 205, 206, through the delivery of differing levels of potential differences, may act as a microheater to concentrate aqueous solutions, and may also act as traditional electrodes to complete an analog circuit, causing confinement and energization of microplasma discharge 208 adjacent to the ends of electrodes 205, 206. Electrodes 205, 206 thus comprise highly conductive materials for carrying electrical signals from power source 107 to energize aqueous sample 211 and nanoparticles 202 within reservoir 203, including but not limited to metals such as chrome, copper, titanium and platinum, patterned onto the surface of substrate 210 by methods known in the art, and as described below. It is preferable that electrodes 205, 206 be constructed from metals with a significant resistance to electroplating, as the potential for some transfer of metal atoms from the electrodes into the microplasma may contaminate the spectral emissions data. It is further preferable that electrodes 205, 206 are fabricated in a manner that withstands intense heat as may be produced by microplasma discharge 208. When a potential difference is applied from power source 107, electrodes 205, 206 first serve as a microheater to evaporate the water within aqueous sample 211. Power source 107 comprises any device known in the art to supply a potential difference across the ends of cathode 205 and anodes 206 of up to 3000 volts. Because of the small scale of the device of the present invention, power source 107 preferably comprises a 12 volt lithium ion battery connected to a high voltage converter that is light weight, consumes low power, and has a wide temperature range (e.g., EMCO High Voltage Corp. Model Q50N-5 (0.125 in$^3$ 5 kV)). In embodiments comprising a microheater as shown in FIGS. 4-6, anodes 206 may comprise several metal wires or leads creating separate circuits with cathode 205 to effectively provide for effective evaporation. In operation, the potential difference applied to cathode 206 and anodes 205 to concentrate aqueous solution 211 is preferably between 12-100 volts (12-100 V). Once the aqueous sample is concentrated using electrodes 205, 206 as a microheater, or if the sample arrives at the diagnostic system 020 previously pre-concentrated, a second potential difference of up to 3000 volts, preferably between 150 volts and 3000 volts, or any range therein, may be applied by power source 107 across the ends of cathode 205 and one of anodes 206 to form one analog circuit.

In one embodiment of the present invention, nanoparticles 202 comprise silica oxide microparticles ball-milled from commercial off-the-shelf larger particles. In other embodiments, nanoparticles 202 may comprise polymers, ceramics, silica, glass or other materials known in the art to adequately form nanoparticles 202 suitable for doping microplasma discharges 208.

Referring now to FIGS. 5(*a*)-5(*e*), an on-chip microplasma diagnostic system 020 may be fabricated as described herein. In this embodiment, substrate 210 may comprise at least two layers of glass sheets. Microheater sheet 226 may preferably measure about fifteen square millimeters (15 mm$^2$) in surface area and about one millimeter (1 mm) in thickness. Sheet 226 further may comprise a layer of chrome coating, typically applied by a thermal evaporation method, as is known in the art. Microheater sheet 226 may then be rinsed in acetone to remove dirt that may have accumulated on the surface of the chrome layer. Microheater sheet 226 may be placed inside a photoresist spinning machine, and a layer of photoresist (e.g., Microposit S1813 Photoresist, Shipley Co., Marlborough, Mass.) applied to the surface of the chrome layer. Microheater sheet 226 may be spun at 4000 rpm for forty-five seconds (45 s) to ensure an even coating of photoresist throughout the entire surface, approximately one micron (10 thick. Sheet 226 may then be baked at ninety degrees Celsius)(90° for 180 seconds (180 s) to harden the photoresist layer. After cooling, a mask pattern, shown in FIG. 5(*e*), may be placed over the substrate and a five minute exposure of ultraviolet light source applied. During the exposure, the areas of the photoresist layer exposed to the ultraviolet light weaken, while the unexposed portions remain intact. Sheet 226 may be baked at 110 degrees Celsius)(110° for 150 seconds (150 s). After cooling, the photoresist layer may be developed in a bath of photoresist developer (e.g., Microposit MF-319 Photoresist Developer, Shipley Co., Marlborough, Mass.). The weakened photoresist layer may be removed, leaving the hardened photoresist behind in the form of the image of the mask, as desired. Sheet 226 may then be cleaned in a bath of water and dried with compressed air. Once dry, sheet 226 may be immersed in a bath of chrome etch to remove the areas of the chrome layer not covered with photoresist. During this immersion, all photoresist remaining on the surface of sheet 226 may also be removed. Sheet 226 may then be cleaned again in a bath of water and dried with compressed air. The chrome remaining on the surface of sheet 226 in the form of a mask, like one shown in FIG. 5(*e*), provides patterned electrical leads to the embodiments described herein. The second glass layer, sheet 227, also may measure about fifteen square millimeters (15 mm$^2$) in surface area and about one millimeter (1 mm) in thickness. A sandblaster then may etch a 15-20 millimeter (15-20 mm) square aperture into sheet 227 to form reservoir 203. Sheet 227 may be adhered to microheater sheet 226 with epoxy or other adhesive as are known in the art such that reservoir 203 is formed with electrodes 205, 206 exposed through the square aperture. In some embodiments, as shown in FIG. 5(c), an additional glass sheet 228 may be etched with a sandblaster to form two small apertures, one aperture 215 for water sample delivery and the other aperture 216 for transmission of emission spectra to fiber optic cable 214. In those embodiments utilizing a third glass sheet 228, sheet 228 may be adhered to sheet 227 with epoxy or other adhesive as are known in the art such that aperture 215 allows for delivery of aqueous sample 211 into reservoir 203 and aperture 216 allows attachment of fiber optic cable 112 for transmission of spectral emission 209 or other measurement or analytical system as is known in the art. The cross-section of a fully assembled three-layer on-chip diagnostic system 020 is shown in FIG. 5(d). The cross-section of a fully assembled two-layer on-chip diagnostic system 020 is shown in FIG. 5(e). In use, an open two-layer device may be preferable for some applications.

In operation, as shown in FIGS. 4(a)-(d), aqueous sample 211, taken from a water source to be tested for contaminants or impurities, may be placed inside reservoir 203. Approximately 0.01 grams (0.01 g) or 10 parts per million (10 ppm) of silica ($SiO_2$) nanoparticles 202 may be mixed into the sample reservoir 203 and thereafter bond with the contaminants to form a nanoparticle-contaminant complex 212. A direct current negative bias of about 12-100 volts (12-100 V) is applied by power source 107 to electrodes 205 and 206, which act as a microheater to energize aqueous sample 211 and evaporate water from solution 211, leaving within reservoir 203 a concentrated mixture 212 of nanoparticles 202 and contaminants (as shown in FIG. 4(b)). A direct current negative bias of up to 3000 volts, preferably about 300 volts to 1500 volts or a range therein, may then be applied by power supply 107 to electrodes 205, 206, which induces an arc of microplasma discharge 208 between cathode 205 and anode 206 (as shown in FIG. 4(c)). The negatively-charged contaminant particle-nanoparticle complexes 212 levitate into the glow region and become a constituent of microplasma 208, altering the spectral emission 209 of discharge 208 (as shown in FIG. 4(d)). Utilizing fiber optic cable 112, the intensity of spectral emission 209 as a function of wavelength may be measured with spectrometer 113. In this manner, contaminants in aqueous sample 211 may be identified by referring to atomic and molecular spectra data tables. Varying the gaseous pressure of the sample reservoir 203 from atmosphere to vacuum allows for both atomic and molecular contaminant spectral emissions 209 to be detected. For example, as ambient pressure is reduced to a vacuum, negatively charged contaminants may be enveloped by a microsheath that scatters free electrons but permits positively charged oxygen and nitrogen atoms to continuously oxidize and reduce the contaminant particles, producing spectral emission 209. In this manner, on-chip water diagnostic system may identify concentrations of atomic and molecular components by varying the gaseous pressure level within the device.

Figure 8:
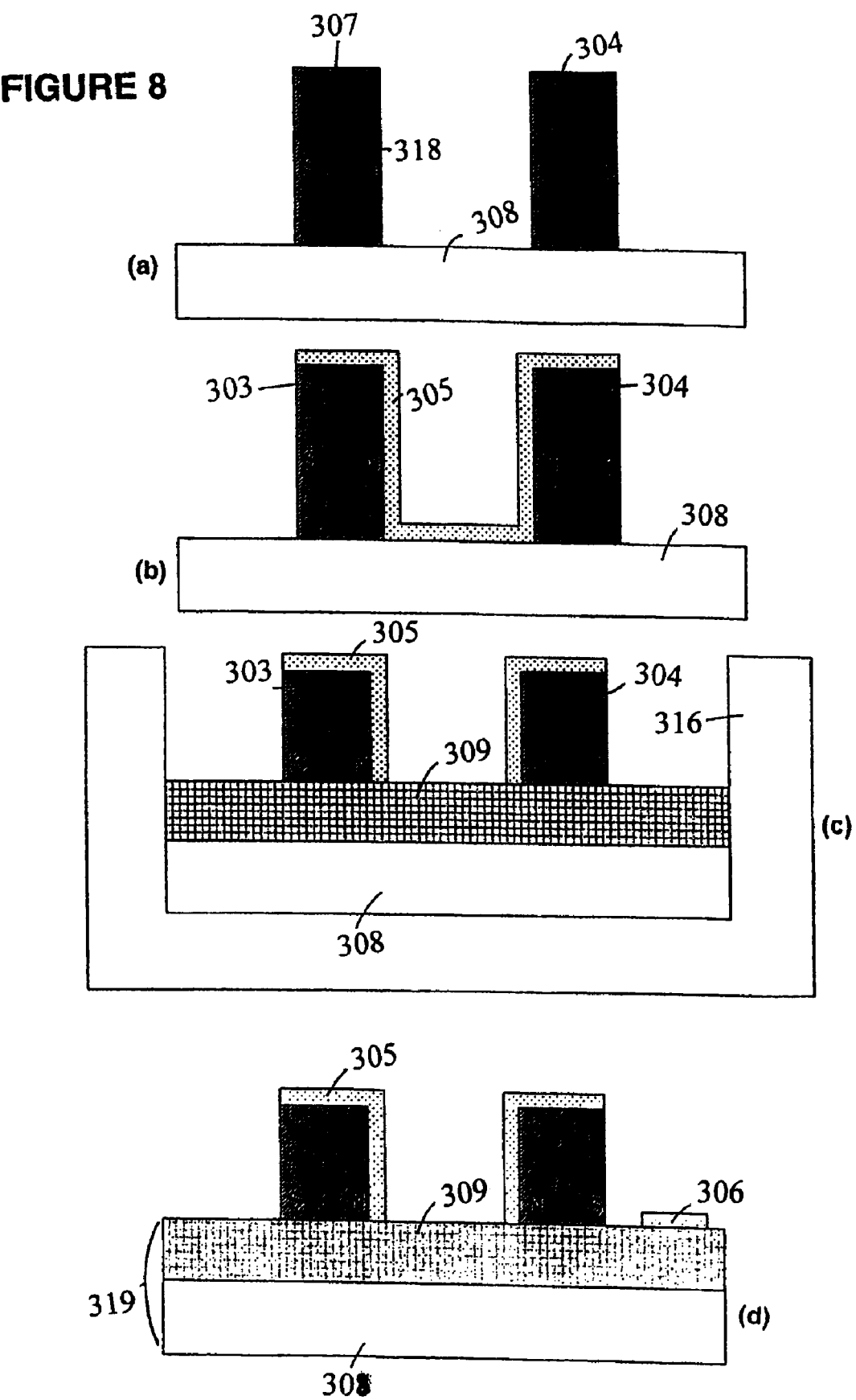
FIGS. 8(a)-8(d) are schematic drawings for fabricating one embodiment of the present invention comprising an on-chip gas detector.

FIGS. 7 and 8(a)-(d) illustrate yet another embodiment of the present invention. An on-chip gas detector comprises a housing 301, electrodes 305, 306, micromagnets 303, 304, and power supply 107. In some embodiments, housing 301 is formed from substrate 319 alone. In other embodiments, housing 301 may generally comprise substrate 319 enclosed within a vacuum chamber 311 (as shown in FIG. 7). Vacuum chamber 311 further comprises a vacuum pump 312 (as generally shown in FIG. 7). Preferably, vacuum chamber 311 is approximately 1 cubic foot (1 $ft^3$) in volume and has through-ports for connections to power supply 107. Substrate 319 may further comprise a glass sheet 308 and an epoxy substrate 307 in which micromagnets 303, 304 are embedded. Micromagnets 303, 304 preferably are formed from niobium/iron epoxy composite as is known in the art, and preferably provide 0.7 Tesla (0.7 T) of magnetic field strength at their surfaces. Micromagnets 303, 304 are positioned within substrate 319 such that the north poles 317, 318 of micromagnets 303, 304, respectively, oppose each other across a distance of about 1.2 millimeters (1.2 mm), as shown in FIG. 8(a).

Hollow cathode 305 is formed between poles 317, 318 of micromagnets 303, 304. Anode 306 is positioned on the surface of substrate 319 remote from hollow cathode 305, for example, about 2-8 millimeters (2-8 mm) from the base of micromagnet 304, as shown in FIG. 8(d). Hollow cathode 305 and anode 306 generally comprise highly conductive materials for carrying electrical signals from power source 107 to energize gas sample 320, including but not limited to metals such as chrome, copper, titanium and platinum, patterned onto the surface of micromagnets 303, 304 and substrate 319 by methods known in the art, and as described below. It is further preferable that electrodes 305, 306 are fabricated in a manner that withstands intense heat as may be produced by microplasma discharge 308. When a potential difference is applied from power source 107, cathode 305 and anode 306 complete an analog circuit. Power source 107 comprises any device known in the art to supply a potential difference across cathode 305 and anode 306 of up to 3000 volts. Because of the small scale of the device of the present invention, power source 107 preferably comprises a 12 volt lithium ion battery connected to a high voltage converter that is light weight, consumes low power, and has a wide temperature range (e.g., EMCO High Voltage Corp. Model Q50N-5 (0.125 $in^3$ 5 kV)). In operation, the potential difference applied to hollow cathode 305 and anode 306 is up to 3000 volts, preferably a voltage between 300 volts and 1500 volts (or any range therein). Referring now to FIGS. 8(a)-(d), an on-chip gas detector 030 comprising micromagnets 303, 304 may be fabricated as described herein. Micromagnets 303, 304 may be fabricated by mixing niobium-iron nanoparticles (made from commercially available off the shelf niobium-iron alloy materials, or purchased in nanoparticle form) and epoxy resin into rectangular molds, then applying a strong magnetic field to reorient the niobium-iron nanoparticles and produce a permanent magnetic field. It should be understood that micromagnets 303, 304 may be fabricated in any manner as is known in the art, or may be commercially available (e.g., Niobium-iron-boron magnets, McMaster-Carr, Chicago, Ill.), preferably prismatic and approximately 1 millimeter (1 mm) by 2 millimeters (2 mm) by 3 millimeters (3 mm) in dimension. A glass sheet may be used as the base layer for substrate 319. As shown in FIG. 8(a), micromagnets 303, 304 may be placed onto glass sheet 308 and preferably fixed in place with epoxy or any other conventional adhesive. A patterned metal layer may then be applied to the top and faces of micromagnets 303, 304, and the surface of glass substrate 308, as shown in FIG. 8(b), to form a continuous hollow cathode 305. Although hollow cathode 305 is shown in FIG. 8(b) coating the top and north faces of the surface of micromagnets 303, 304, hollow cathode 305 also may coat the top, north and south faces of each micromagnet 303, 304, or the entirety of the exposed surfaces (i.e., all non-embedded surfaces of all faces) of the micromagnets 303, 304. Once patterned metal layer is applied, glass sheet 308 and micromagnets 303, 304 may be placed into Teflon mold 316, and epoxy or other conventional resin may be injected into mold 316 to form an epoxy layer 307 as shown in FIG. 8(c). Although epoxy layer 307 should cover the portion of hollow cathode 305 stretching between micromagnet 303 and micromagnet 304, epoxy layer 307 need not fill Teflon mold 316, rather, epoxy layer 307 may preferably be about 9.5 millimeters (9.5 mm) deep. As shown in FIG. 8(d), Teflon mold 316 may be removed and a metal anode may be patterned onto the surface of epoxy layer 307 near micromagnets 303, 304. Gas detector 020 may then be placed into a vacuum chamber 311 with throughports for power supply 107 and gas sample delivery system 310, as shown in FIG. 7.

Referring to the embodiment shown in FIG. 7, in operation, vacuum chamber 311 of gas detector 030 receives gas sample 320 from gas sample delivery system 310. A direct current negative bias of about 350 volts to about 1500 volts, or any range therein, is applied by power source 107 to electrodes 305 and 306 to create a magnetically confined microplasma discharge 321 within the region of magnetic field between micromagnets 303 and 304. Micromagnets 303, 304 create circular magnetic fields at their top faces where the corresponding electric field is highest, confining electrons in this region to circular orbits, thus increasing ionization of the surrounding gas. The corresponding spectral emission 322 from microplasma discharge 321 may then be transmitted through fiber optic cable 112 to spectrometer 113, where the intensity of the spectral emission 322 as a function of wavelength is transmitted to and/or analyzed by end-use equipment, such as microprocessors, computers, and the like. As the pressure within the vacuum chamber changes from atmospheric pressure to a vacuum pressure using vacuum pump 312, electron energy may be decreased to optimize the spectral intensity of different gasses. For example, when alcohol vapor is introduced through gas delivery system 310, characterization of emission spectra 322 from microplasmic discharge 321 allows for measurement of the alcohol's molecular constituents, as well as of nitrogen within the background gas.

Figure 9:
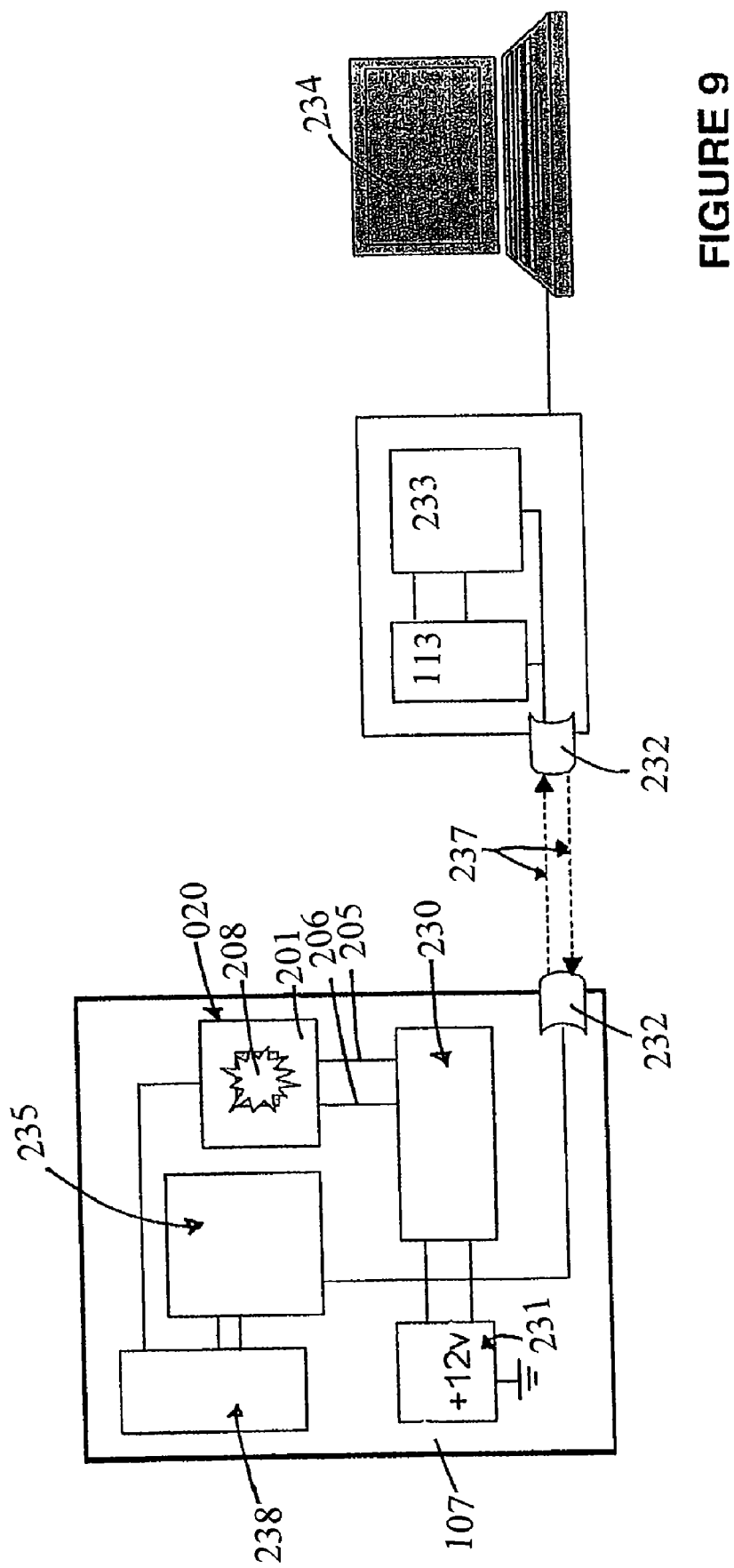
FIG. 9 is a schematic drawing of one embodiment of the present invention in operation.

Referring now to the embodiment shown in FIG. 9, an on-site kit 250 comprising on-chip diagnostic system 020, as described more fully above, is illustrated as may generally be utilized in the field. In this embodiment, on-site kit 250 comprises housing 201, electrodes 205, 206, power supply 107, fiber optic cable 112, data sampler 238, wireless transmitter 235, and an antenna 232. Referring still to FIG. 9, power supply 107 further comprises twelve volt (12 V) lithium ion battery 231 and high voltage converter 230. Lithium ion battery 231 may be connected to ground. Power supply 107 supplies direct current negative bias voltages, as described above, to electrodes 205, 206 to evaporate aqueous samples delivered to housing 201, leaving negatively-charged contaminants bound to nanoparticles, also as described above, and to confine and energize microplasma discharge 208 containing contaminant-nanoparticle complexes. In this embodiment, receiving antenna 232, spectrometer 113, digital signal processor 233 and microprocessor 234 may be remote from on-site kit 250 such that on-site diagnostics (i.e., diagnostics to be accomplished at water treatment plants, natural water sources, and the like) may be accomplished using a small device such as on-site kit 250, and data obtained may be digitally converted and analyzed at a different location where large scale devices such as spectrometer 113 and microprocessor 234 may be used (i.e., laboratories, corporate headquarters, and the like). In operation, spectral emission 209 from microplasma discharge 208 may be transmitted via fiber optic cable 112 to data sampler 238, which allows for transmission of data signal 237 by wireless transmitter 235 to spectrometer 113 utilizing antennas 232. Streaming data signal 237 may be transferred from antenna 232 within on-site kit 250 to antenna 232 off-site, which then transmits the data to spectrometer 113. Spectrometer 113 analyzes spectral emission 209, and optionally transmits the resulting data, including intensity of emission as a function of wavelength, to a digital signal processor 233, which in turn communicates with an end-user device such as a microprocessor, computer, laptop, workstation or other device capable of displaying results and/or processing data as directed by a user. In other embodiments, on-site kit 250 may transmit spectral emission 209 directly to spectrometer 113 via fiber optic cable 112. Although system 020 is shown in operation in FIG. 9, it should be appreciated by those in the art that an on-chip ultraviolet light source 010 and accompanying reservoir for tagging dye and biomolecules (as shown in FIG. 3) may be substituted for system 020 within on-site kit 250 such that field operation may be accomplished in a similar manner. Likewise, gas detector 030 may be substituted for system 020 within on-site kit 250 in a similar manner.

In some embodiments, as shown in FIG. 9, the on-site kit 250 comprising system 020 may be contained in one rugged container with a convenient receptacle for water samples. This type of on-site device may run for longer periods of time on electrical energy stored in battery 231 if only those components required for testing an aqueous sample, and for recording and transmitting those results are included within the on-site kit 250. On-site kit 250 will also be more compact and discrete if fewer components are included, allowing for mounting or positioning in a wider range of placements in the field.

Once fully assembled, embodiments of the present invention, as described above, may be coated with black powder-coating epoxy for insulation of optics and electronics. These embodiments also may be further packaged within rigid metal containers with all electrical circuits grounded to the packaging, and if necessary, to an earth ground. In some embodiments, vacuum chamber 311 may also be contained within a rigid metal container to prevent broken glass or other sharp objects from protruding from the systems. Although the circuitry of electrodes 105, 106, 205, 206 and 305, 306 has been described in a simplistic manner, all circuitry energizing microplasma discharges may be designed in a more sophisticated manner, for example, to automatically shut-off the power supply 107 in the event that a fire or electrical short is detected or in the event that a breach is found in the housings.

Although certain preferred embodiments have been described above, it will be appreciated by those skilled in the art to which the present invention pertains that modifications, changes, adaptations, and improvements may be made without departing from the spirit of the invention defined by the claims. For example, although the electrodes have been described generally as metal, other embodiments of the present invention may utilize chrome, copper, titanium, platinum or other metals within the spirit of the invention. Moreover, the electrodes may be patterned onto the housings or substrates as described above. In the same manner, the power source generally described herein may provide a direct current negative bias voltage of up to 3000 volts, but preferably, the voltage used to create a microplasma discharge between the electrodes may range between approximately 300 volts and approximately 1500 volts. The user may select any voltage in this range and still achieve successful results. As described above, the gaseous pressure within the interior of the housing should be controlled, preferably by a vacuum pump in fluid communication with the interior of the housing. Moreover, the light source of the present invention is envisioned to comprise a reservoir holding tagging dye (e.g., 7-methoxycoumerin-3-carboxylic acid dye) bound to biomolecules, a spectrometer and at least two fiber optic cables, wherein the dye reservoir receives ultraviolet spectra from the nanoparticles through a first fiber optic cable, and emits fluorescent spectra through a second fiber optic cable to the spectrometer. Further, the light source of the present invention may be presented in embodiments with a purality of cavities, in which case a runner anode may be used to energize each reservoir's anode such that voltage is efficiently provided to each cavity at one time to generate a microplasma discharge as described above, and such runner anode, a plurality of anodes, and a plurality of cathodes may be patterned electrical leads as well as traditional electrical wiring. In some embodiments, the runner anode may be patterned onto the interior surface of the glass sealing layer, each cathode may be patterned onto the surface of the glass substrate and each anode may be patterned onto the surface of the glass substrate such that each is engaged with at least two reservoirs.

In the same manner, it should be appreciated that the present invention encompasses methods related to the devices described herein. Specifically, the present invention provides a method of producing light, comprising the steps of: a) depositing a plurality of nanoparticles within a housing; b) supplying power to at least two electrodes engaged with the nanoparticles; and c) controlling the level of gaseous pressure within the housing. This method may utilize nanoparticles made from metal oxide, including but not limited to chromium oxide, iron oxide, or copper oxide, glass, silica oxide, polymers or ceramics. Also, the gaseous pressure within the housing may be controlled by a vacuum pump in fluid communication with the interior of the housing. The electrodes used in this method of producing light may also comprise at least one anode and at least one cathode, and a direct current negative bias voltage of up to 3000 volts, preferably a voltage in the range of approximately 300 volts to approximately 1500 volts, may be supplied to the electrodes to create a microplasma discharge.

It should be further understood that although the micromagnets of embodiments of the present invention used to detect gas, as described above, may be placed any distance apart such that the direct current negative voltage applied to the anode and the hollow cathode formed on the surface of the micromagnets creates a confined microplasma discharge, preferably the poles of the micromagnets may be positioned at least 0.1 mm apart and up to 20 mm apart to maintain a confined discharge. Magnets may be fabricated using any known or future developed method, but preferably may comprise niobium-iron epoxy composite and preferably may be sized approximately 1 mm by 2 mm by 3 mm. The patterned layer of metal used to form the hollow cathode and the anode may be constructed of any metal, preferably copper. The gaseous pressure surrounding the magnets may be controlled using a vacuum pump in fluid communication with the housing or any other means as is known in the art, and a gas sample for detection may be delivered to the gas detector using a through-port within the housing or any other means as is known in the art.

The present invention further provides a method for detecting gas comprising the steps of a) delivering a gas sample to a housing, the housing comprising a substrate, at least two magnets engaged with the substrate, a cathode comprising a patterned layer of metal coating at least one surface of each magnet, and a metal anode positioned on the substrate and remote from the magnets; b) supplying power to the cathode and the anode; c) selectively controlling the gaseous pressure within the housing to a desired pressure; and d) detecting with a spectrometer atomic and molecular emissions. This method may utilize a vacuum pump in fluid communication with the interior of the housing to control the gaseous pressure of the interior of the housing. The electrodes used in this method of detecting gas may comprise a hollow cathode formed on exposed surfaces of the magnets, and a remote anode, preferably an anode positioned near but not touching the magnets, and a direct current negative bias voltage of up to 3000 volts, preferably a voltage in the range of approximately 300 volts to approximately 1500 volts, may be supplied to the electrodes to create a microplasma discharge.

The present invention further provides for a water diagnostic device as described above, wherein the electrodes may be understood to encompass any material that is conductive, including metals, such as copper, chrome, platinum and the like. The electrode may also be patterned onto the housing as described above, but may also encompass placement upon the substrate of the device in any manner that is known or future developed in the art such that the direct current negative bias voltage may be applied to the region in which a microplasma discharge is desired though a cathode and an anode, or other variations of electrodes as are well known in the art. In embodiments providing a water diagnostic device, the electrodes serve to deliver a first voltage of up to 12 volts, preferably a voltage in the range of approximately 12 volts to approximately 100 volts, to preconcentrate the sample (i.e., evaporate the aqueous sample) and a second voltage of up to 3000 volts, preferably a voltage in the range of approximately 300 volts to approximately 1500 volts, to create a microplasma discharge as better described above. The present invention also provides for a method for detecting contaminants in aqueous solution, comprising the steps of a) delivering an aqueous sample to a transparent housing, the housing comprising a plurality of nanoparticles positioned within the housing; b) supplying power to at least one cathode and at least one anode to remove moisture from the sample and to energize the nanoparticles; c) selectively controlling the gaseous pressure within the housing to a desired pressure; and d) detecting with a spectrometer atomic and molecular emissions. This method may utilize a vacuum pump in fluid communication with the housing to selectively control the gaseous pressure within the housing.

It should be further understood that the embodiments of the present invention may be utilized in combination with at least one fiber optic cable in communication with a spectrometer, wherein the cable receives light from the device, whether for detecting gas or contaminants in water or fluorescence from tagged biomolecules, all as described above, and the spectrometer provides communicates spectral analysis from the light and transmits this analysis to the user via a processing system, such as a digital signal processor, a microprocessor, a computer, or similar component.

Within the scope of the present invention, an on-chip diagnostic kit may be assembled comprising, (a) an on-chip diagnostic device comprising a housing capable of receiving an aqueous sample, a plurality of nanoparticles positioned within the housing, a means for removing moisture from the sample and for energizing the nanoparticles, and a means for controlling the gaseous pressure within the housing; (b) a spectrometer; (c) a means for transmitting light from the housing to the spectrometer; and d) a means for communicating spectral analysis from the light from the spectrometer to a user. Other embodiments of an on-chip diagnostic kit may be assembled comprising, (a) an on-chip gas detector comprising a substrate, at least two magnets engaged with the substrate, a means for energizing the area adjacent to the magnets, and a vacuum chamber surrounding the magnets and the substrate; (b) a spectrometer; (c) a means for transmitting light from the housing to the spectrometer; and d) a means for communicating spectral analysis from the light from the spectrometer to a user. Lastly, other embodiments of an on-chip diagnostic kit may be assembled comprising (a) an on-chip ultraviolet light source comprising a housing, a plurality of nanoparticles within the housing, a means for energizing said nanoparticles, and a means for controlling the gaseous pressure within the housing; (b) a separate reservoir containing biomolecules associated with tagging dye; (c) a spectrometer; (d) a means for transmitting light from the housing to the reservoir, and from the reservoir to the spectrometer; and d) a means for communicating spectral analysis from the light from the spectrometer to a user. Each of these on-chip diagnostic kits may be contained with a rugged container and may present wireless elements such that the spectrometer and/or means for communicating spectral analysis from the spectrometer may receive data or light from the rugged container in a location remote from the rugged container.

Accordingly, all such modifications, adaptations, changes, and improvements are intended to come within the scope of the present invention.

We claim:

1. An on-chip light source, comprising:
    a housing,
    a plurality of nanoparticles within the housing,
    a means for energizing said nanoparticles,
    a means for controlling the gaseous pressure within the housing,
    a reservoir containing a tagging dye bound to biomolecules,
    a spectrometer and
    at least two fiber optic cables, wherein the dye reservoir receives ultraviolet spectra from the nanoparticles through a first fiber optic cable, and emits fluorescent spectra through a second fiber optic cable-to the spectrometer.

2. The light source of claim 1 wherein the nanoparticles comprise a material selected from the group consisting of metal oxide, silica oxide, polymer and ceramic.

3. The light source of claim 2 wherein the metal oxide is selected from the group consisting of chromium oxide ($Cr_2O_3$), copper oxide (CuO), and iron oxide ($Fe_2O_3$).

4. The light source of claim 1 wherein the means for energizing the nanoparticles comprises at least two electrodes connected to a power source.

5. The light source of claim 4 wherein the electrodes are metal.

6. The light source of claim 4 wherein the power source provides a direct current negative bias voltage of up to 3000 volts to the electrodes.

7. The light source of claim 1 wherein the means for controlling gaseous pressure comprises a vacuum pump in fluid communication with the interior of the housing.

8. The light source of claim 1 wherein the housing comprises a plurality of reservoirs within a glass substrate and a glass sealing layer, wherein the nanoparticles are contained within each reservoir.

9. The light source of claim 8 wherein the means for energizing the nanoparticles comprises a plurality of anodes, and a plurality of cathodes, such that power may be selectively applied to one or more reservoirs to energize the nanoparticles therein.

10. The light source of claim 9 further comprising a runner anode, the runner anode engaged with each anode such that power may be applied to the runner anode to energize each anode.

11. The light source of claim 1 wherein the means for energizing comprises at least one anode and at least one cathode, a power source, and wherein the means for controlling the gaseous pressure comprises a vacuum pump in fluid communication with the interior of the housing.

12. An on-chip diagnostic device comprising a housing, an aqueous sample positioned within the housing, a plurality of nanoparticles positioned within the housing, a means for removing moisture from the sample and for energizing the nanoparticles, a means for controlling the gaseous pressure within the housing, and at least one fiber optic cable in communication with a spectrometer, wherein the cable receives transmitted light from the device.

13. The device of claim 12 wherein the housing comprises a glass substrate with a reservoir, the nanoparticles positioned within the reservoir.

14. The device of claim 13 wherein the power source provides a direct current negative bias voltage in the range from about 300 to about 1500 volts to the electrodes.

15. The device of claim 12 wherein the means for controlling the pressure within the housing comprises a vacuum pump.

16. The device of claim 12 wherein the means for removing moisture from the sample and for energizing the nanoparticles comprises at least two electrodes connected to a power source.

17. The device of claim 12 wherein the nanoparticles comprise material selected from the group consisting of silica oxide, ceramic and polymer.

* * * * *